(12) United States Patent
Bossenmaier et al.

(10) Patent No.: US 9,339,560 B2
(45) Date of Patent: May 17, 2016

(54) METHOD FOR DETERMINING THE ANTI-TUMOR EFFICACY OF MONOCLONAL ANTIBODIES

(75) Inventors: Birgit Bossenmaier, Seefeld (DE); Valeria Lifke, Penzberg (DE); Werner Scheuer, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 14 days.

(21) Appl. No.: 13/061,770

(22) PCT Filed: Sep. 21, 2009

(86) PCT No.: PCT/EP2009/006781
§ 371 (c)(1),
(2), (4) Date: Mar. 2, 2011

(87) PCT Pub. No.: WO2010/031578
PCT Pub. Date: Mar. 25, 2010

(65) Prior Publication Data
US 2011/0165082 A1    Jul. 7, 2011

(30) Foreign Application Priority Data

Sep. 22, 2008    (EP) ...................................... 08016610

(51) Int. Cl.
*A61K 39/395* (2006.01)
*A61K 49/16* (2006.01)
*A61K 49/00* (2006.01)
*C07K 16/32* (2006.01)
*A61K 39/00* (2006.01)

(52) U.S. Cl.
CPC ............. *A61K 49/0008* (2013.01); *C07K 16/32* (2013.01); *A61K 2039/505* (2013.01); *A61K 2039/5152* (2013.01); *A61K 2039/5156* (2013.01); *A61K 2039/545* (2013.01)

(58) Field of Classification Search
None
See application file for complete search history.

(56) References Cited

U.S. PATENT DOCUMENTS

2006/0172350 A1* 8/2006 Mather et al. ................ 435/7.23

FOREIGN PATENT DOCUMENTS

WO    WO 03/083072    * 10/2003

OTHER PUBLICATIONS

Staquet et al, Hybridoma, 2006, 25:68-74.*
Saffran et al, PNAS, 2001, 98:2658-2663.*
Trikha et al, Int J Cancer, 2004, 110:326-335.*
Larbouret et al, Clin Cancer Res, Jun. 2007, 13:3356-3362.*

* cited by examiner

*Primary Examiner* — Mark Halvorson

(57) ABSTRACT

The present invention relates to a method for determining the anti-tumor efficacy of monoclonal antibodies in pre-clinical rodent testings and the use of said method for the reduction of side testings.

2 Claims, 3 Drawing Sheets

METHOD FOR DETERMINING THE ANTI-TUMOR EFFICACY OF MONOCLONAL ANTIBODIES

The present invention relates to a method for determining the anti-tumor efficacy of monoclonal antibodies in preclinical rodent testings and the use of said method for the reduction of side testings.

BACKGROUND OF THE INVENTION

Monoclonal antibodies for therapeutic cancer treatment undergo a costly and time-consuming evaluation procedure. Usually they are derived by e.g. immunization with the respective tumor antigen or fragments thereof, which yields hybridomas producing monoclonal antibody against the tumor antigen. Before further intensive evaluation a time-consuming purification procedure has to be performed after which they are evaluated first in vitro, and then in preclinical animal studies. In the in vitro studies mainly their binding affinity to the respective tumor antigen and the growth inhibition on human tumor cells is determined, which is a prerequisite for preclinical animal testings. However, it has been shown, that the in vitro tumor cell growth inhibition does not always correlate with the efficacy in the in vivo xenograft animal studies. It has been shown, that antibodies which have good antiproliferative activity in vitro, can be totally inactive in the preclinical in vivo model, while in vitro inactive antibodies can execute significant in vivo efficacy. Therefore, in general the preclinical animal testings for such antibodies is extensive and time consuming, and a lot of different antibodies have to be tested because of the poor predictive potential of the in vitro studies. A reduction of preclinical animal testing and also a less time-consuming procedures is therefore one important task in the development of monoclonal antibody against the tumor diseases.

Staquet and Giles-Komar (Hybridoma 2006; 25: 68-74) describe a method of the in vivo evaluation of monoclonal antibodies. They injected hybridomas in matrigel subcutaneously into mice. Four days later, tumor cells were injected subcutaneously into the same mice, and the tumor growth was measured over time. A reduced tumor growth or no tumor growth in comparison with control hybridomas indicated the antiproliferative efficacy of the monoclonal antibodies produced by the respective hybridomas. With this method it is possible to distinguish anti-tumor active antibodies from non-anti-tumor active antibodies. However, this method allows no or only poor differentiating possibilities between the antiproliferative potential of antibodies, which still have to be purified from the hybridomas and tested again for further evaluation of their antiproliferative potential.

SUMMARY OF THE INVENTION

One aspect of the invention is a method for the determination of the anti-tumor efficacy of a monoclonal antibody comprising the consecutive steps of
  a) application of tumor-cells to a rodent;
  b) measurement of the tumor size of said rodent in dependency of the time until the tumor size exceeds 100 mm$^3$;
  c) application of hybridomas producing said monoclonal antibody to said rodent; and
  d) measurement of the tumor size of said tumor-bearing rodent in dependency of the time.

The method according to the invention is a more rapid and efficient procedure to identify, differentiate and prioritize new therapeutic antibodies with anti-tumor efficacy after immunization compared to conventional testing and prioritization after purification and in vitro preselection.

Another aspect of the invention is the use of said method for the reduction of preclinical testing.

DETAILED DESCRIPTION OF THE INVENTION

One embodiment of the invention is a method for the determination of the anti-tumor efficacy of a monoclonal antibody comprising the consecutive steps of
  a) application of tumor-cells to a rodent;
  b) measurement of the tumor size of said rodent in dependency of the time until the tumor size exceeds 100 mm$^3$;
  c) application of hybridomas producing said monoclonal antibody to said rodent; and
  d) measurement of the tumor size of said tumor-bearing rodent in dependency of the time.

In step a) the application is preferably a subcutaneous, orthotopic or intravenous injection, more preferably subcutaneous injection, the tumor cells are human, the rodent is preferably a mouse or rat, more preferably a mouse.

In step b) the tumor size is measured until the tumor size is between 100 mm$^3$ and 300 mm$^3$.

In step c) the application is preferably a subcutaneous injection of the hybridomas in matrigel, or in hollowfibers, more preferably in matrigel.

Optionally a further step e) in which the rodent is sacrificed and further investigated for side effects is added.

Said monoclonal antibody produced by said hybridomas is an antibody binding to a tumor antigen which is expressed on the cell surface of said tumor cells, which are used in the method according to invention.

The terms "monoclonal antibody" as used herein refer to a preparation of antibody molecules of a single amino acid composition. Such are produced by "hybridomas" after immunization with respective tumor antigens. The antigen may be introduced for immunization into e.g. a mouse or rat or other animals by any suitable means. Preferably, the animal is immunized intrasplenically, intraveneously, intraperitoneally, intradermally intramuscular, subcutaneously alone or in combination with appropriate immunomodulate agents (e.g. CFA). Dose of each antigen should preferably be in the range of between 1-500 µg. The resulting mouse lymphocytes can be isolated and fused with a human- or heteromyeloma cell using PEG or electrofusion based on standard protocols to generate hybridomas. Electrofusion is based upon a reversible structural change of the cell membranes, which is caused by the effects of an electrical field and is applicable for a wide spectrum of cells for fusion of two or more cells of the same or different origins, including their complete structures (nucleus, membranes, organelle, cell plasma) to create a new, viable cell. This result in the in the hybridomas producing monoclonal antibodies, which are suitable for the method according to the invention.

As used herein, the term "binding" or "specifically binding" refers to the binding of the antibody to an epitope of an tumor antigen in an in vitro assay, preferably in a cell-based ELISA with CHO cells expressing wild-type antigen. Binding means a binding affinity ($K_D$) of $10^{-8}$ M or less, preferably $10^{-13}$ M to $10^{-9}$ M. Binding of the antibody to the antigen can be investigated by a BIAcore assay (Pharmacia Biosensor AB, Uppsala, Sweden). The affinity of the binding is defined by the terms ka (rate constant for the association of the antibody from the antibody/antigen complex), $k_D$ (dissociation constant), and $K_D$ ($k_D$/ka).

The method according to the invention represent an improvement over conventional testing of purified antibodies for several reasons (see also Table 1): By prioitization before the antibody purification, only the antibodies most effective, most interesting hybridomas have to be purified for further characterization, which means a significant reduction of the number of antibody purifications, speeds up the development of new therapeutic antibodies, and reduces the general testing efforts necessary for therapeutic antibody development (in comparison if many pruridied antibodies have to be tested). Also antibodies of low producing hybridomas, which are often neglected for further evaluation (the neglection is due to their low production rate in hybridomas, which makes it difficult to get enough purified antibody, and not due their therapeutic properties) are more easily available for evaluation of their therapeutic properties.

TABLE 1

Comparison of Conventional vs. new Hybridoma technology

|  | Conventional technology | New Hybridoma technology |
|---|---|---|
| Time effort for culturing of Hybridoma in vitro | two to three weeks | not necessary |
| Time effort for purification and quantification of mab from Hybridoma supernatants | one week | not necessary |
| Time effort for in vitro assays (2D and 3D proliferation, FACS, BiaCore) | one to two weeks | not necessary |
| Correlation of in vitro effector functions with therapeutic activity in vivo | limited * | — |
| Correlation of therapeutic efficacy of hybridoma with efficay of purified mab | — | high |
| Functionality of tumor-stroma cell interactions | limited * * | given |
| Pharmacokinetic aspects | not possible | yes |
| Number of mice for preclinical efficacy study | 10 for one mab and one dosage multiple applications | 5 for one hybridoma no applications |
| costs | 100% | 20% |
| potential of optimization | difficult | yes |

* Examples exists where mabs had marginal activity on proliferation in vitro, but convincing activity in vivo
* * 3D coculturing possible, but still no proper reflection of the in vivo situation A further aspect of the invention is a method for the reduction of preclinical rodent animal testing, characterized by
  a) using for the evaluation of the anti-tumor efficacy of monoclonal antibodies produced by hybridomas, said method for the determination of the anti-tumor efficacy of a monoclonal antibody described above, and
  b) prioritizing one to three monoclonal antibodies, preferably one monoclonal antibody, for further preclinical evaluation.

Said further preclinical evaluation can be made either in the same or other preclinical animal testings. Using this method of early prioritization only a small number of monoclonal antibody drug candidates has to be evaluated in further preclinical animal testings instead of testing a broad spectrum of purified antibodies broadly in preclinical animal testings. Thus, up to 50% reduction of preclinical animal testings in rodents can be achieved.

The following examples and figures are provided to aid the understanding of the present invention, the true scope of which is set forth in the appended claims. It is understood that modifications can be made in the procedures set forth without departing from the spirit of the invention.

EXAMPLE 1

Effect of Anti-HER3 Antibodies Producing Hybridomas in a Human Lung Tumor Xenograft (Method of Staquet et al.)

Based on the method published by Staquet und Giles-Komar four different hybridomas, which produce antibodies against HER3 have been injected in female BALB/c nude mice. The hybridomas ($5\times10e5$) were mixed with 100 microliter matrigel at 4° C. and immediately injected subcutaneously in the shoulder region. Ag8 cells served as a control. One week thereafter Calu-3 tumor cells ($5\times10e6/100$ microliter), which express the Her3 antigen on the cell surface were injected subcutaneously on the opposite shoulder. Tumor volume was monitored subsequently with a caliper for the following ten days.

Figure 1:
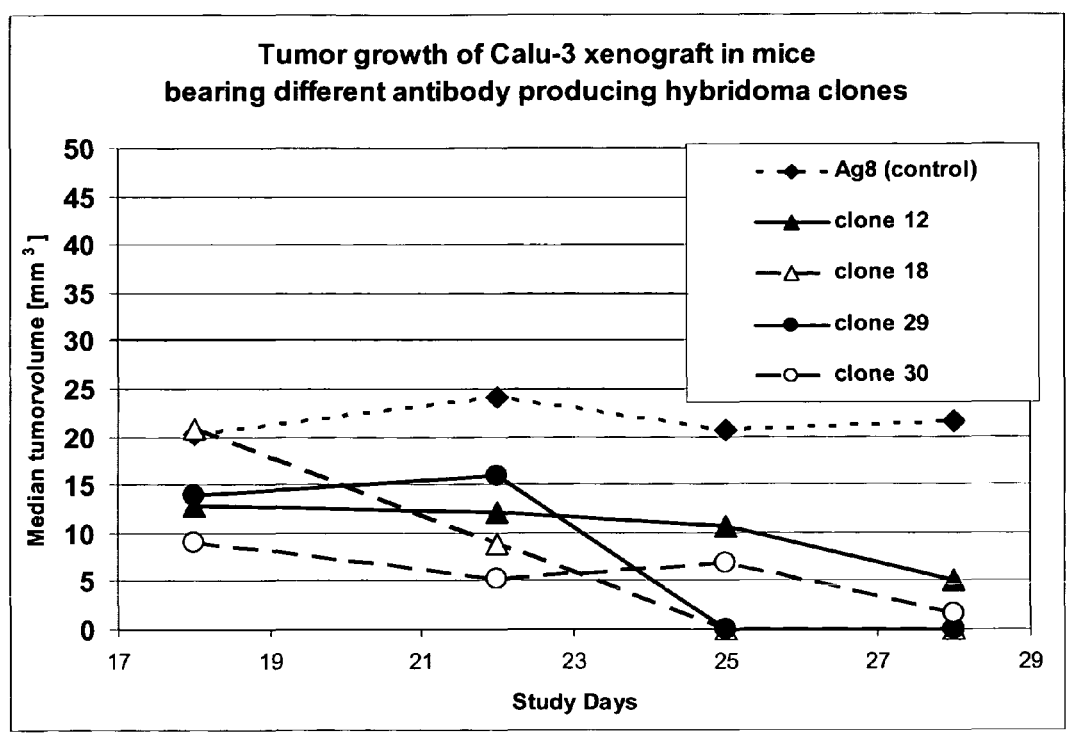
FIG. 1 Effect of antibody producing hybridomas on the tumor growth in a Calu-3 xenograft model when the method according to Staquet et al. (Example 1) is applied.

FIG. 1 indicates that the antibodies secreted from the hybridomas suppress tumor growth. However, based on the tumor volumes measured no differentiation and therefore no prioritization of the different hybridomas regarding the anti-tumoral efficacy can be made.

EXAMPLE 2

Effect of Anti-HER3 Antibodies Producing Hybridoma in a Human Lung Tumor Xenograft (New Optimized Method)

Calu-3 tumor cells ($5\times10e6/100$ microliter) were injected subcutaneously into female Balb/c nude mice. After 44 days tumor carrying mice were randomized and divided into different groups. The mean of the tumor volumes was 130 mm$^3$. In contrast to the method described by Staquet und Giles-Komar, hybridomas producing anti-Her3 antibodies, were mixed with matrigel and injected subcutaneously opposite to the tumor cell injection site. In addition, two hybridoma (clone 31 and clone 33) have been included in this experiment. Again Ag8 cells were used as a hybridoma control.

Figure 2:
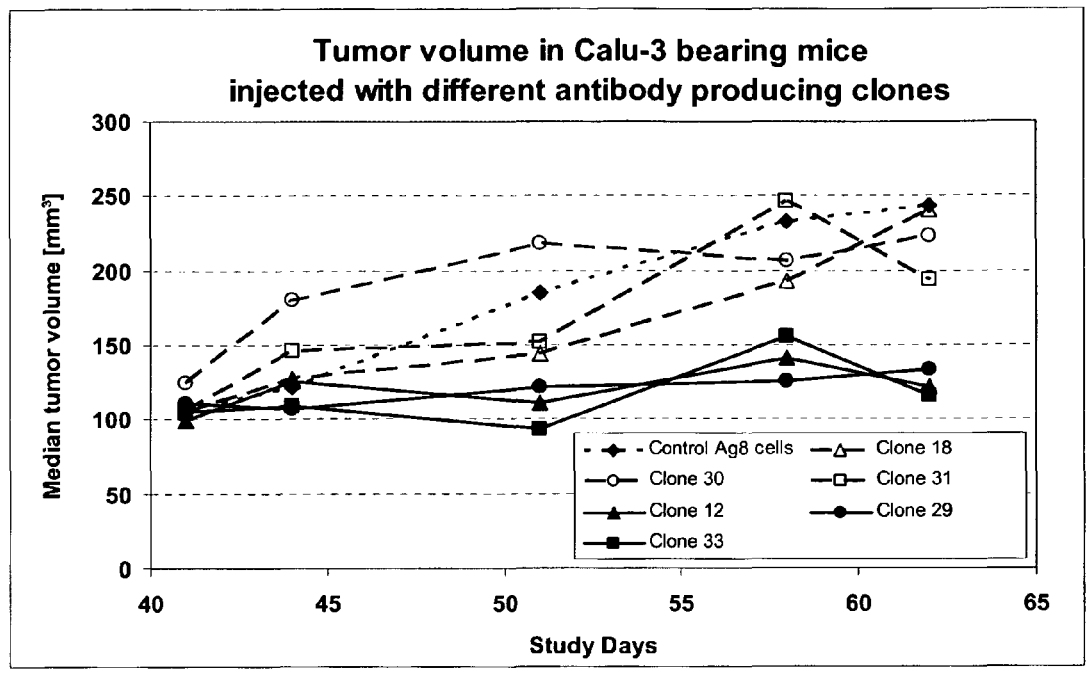
FIG. 2 Effect of antibody producing hybridomas on the tumor growth in a Calu-3 xenograft model in the new method according to the invention (Example 2)

FIG. 2 demonstrates that 23 days after the injection of the hybridomas clone 33, 12 and 29 induce the strongest antitumoral efficacy. In contrast, clone 18, 30 und 31 exerted no effect on the growth of the tumors and as expected the hybridoma Ag8 was ineffective. This optimized method allows a selection of different hybridomas regarding its anti-tumoral efficacy.

Comparison of FIG. 1 with FIG. 2 demonstrates that the new technique is superior to the method described by Staquet and Giles-Komar. This application describes the injection of hybridomas into mice carrying established tumors and therefore conclusions can be drawn regarding the efficacy of the antibodies secreted by the hybridomas reflecting the clinical situation more properly.

EXAMPLE 3

Evaluation of the Anti-Tumoral Efficacy of Antibodies Purified from Hybridoma Supernatants in a Human Lung Tumor Xenograft This example describes the conventional approach for the development of therapeutic antibodies and supports the results of the experiment described in example 2.

Antibodies against the Her3 antigen have been purified from the supernatants of six different hybridomas. These antibodies were tested for the anti-tumoral activity in a relevant xenograft.

Calu-3 tumor cells (5×10e6/100 microliter) were injected subcutaneously into female Balb/c nude mice. After 35 days tumor carrying mice were randomized and divided into different groups. The mean of the tumor volumes was 80 mm$^3$. Mice were treated by i.p. injection with the different antibodies once weekly for 5 weeks Tumor volume was monitored twice weekly with a caliper for the whole study period. Antibodies derived from clone 12 (tumor growth inhibition 66%), antibodies purified from clone 33 (tumor growth inhibition 50%) and antibodies from clone 29 (tumor growth inhibition 47%) were identified as the most effective regarding tumor growth suppression. In contrast antibodies purified from the clones 18, 30 and 31 were ineffective (FIG. 3).

Figure 3:
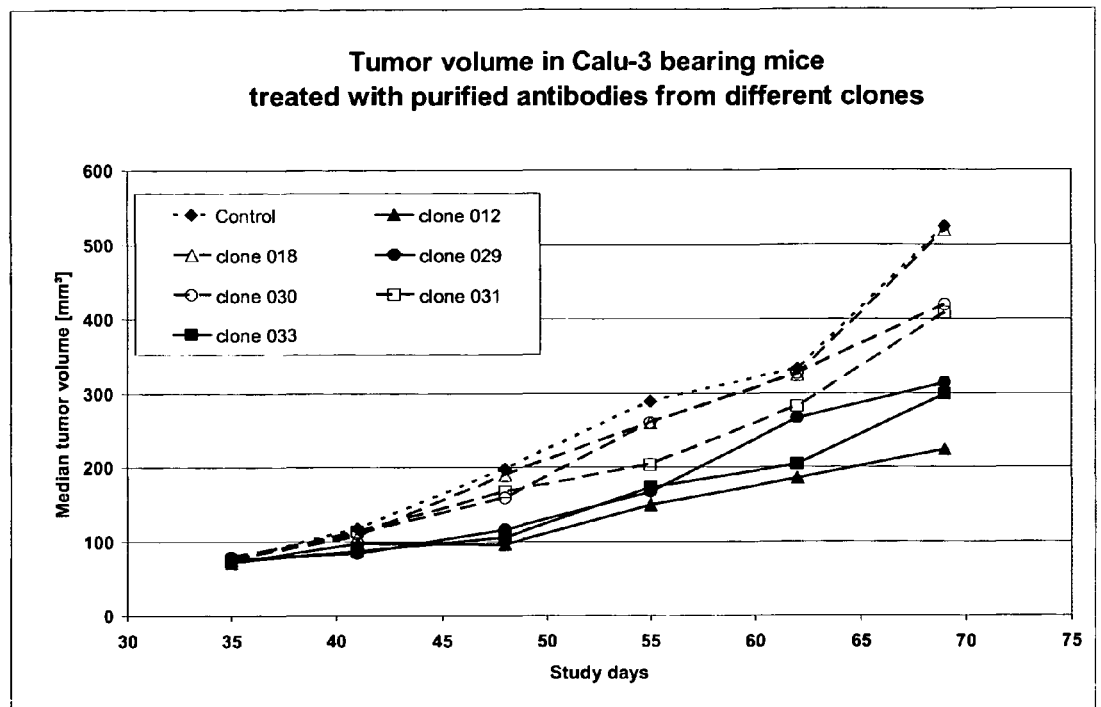
FIG. 3 Effect of the purified antibodies on the tumor growth in a Calu-3 xenograft model in the new method according to the invention (Example 3)

Comparison of FIG. 2 with FIG. 3 demonstrates that hybridomas which have been injected into mice with established tumors exerted an anti-tumoral activity comparable with the therapeutic efficacy of purified antibodies purified from the supernatants of the relevant hybridomas.

Furthermore, for hybridomas which were ineffective, the purified antibodies from these hybridomas did not diminish tumor growth. These results demonstrate the validity of the improved method.

This means a clear reduction in experimental effort for the evaluation of therapeutic antibodies, as the purification is no longer needed for the evaluation and prioritization.

The invention claimed is:

1. Method for testing the anti-tumor efficacy of a monoclonal antibody comprising the consecutive steps of
   a) application of tumor-cells to a rodent;
   b) measurement of the tumor size of said rodent in dependency of the time until the tumor size exceeds 100 mm3;
   c) application of hybridomas producing said monoclonal antibody to said rodent; and
   d) measurement of the tumor size of said tumor-bearing rodent in dependency of the time.

2. Method according to claim 1, characterized in that in a further step
   e) the rodent is sacrificed and further investigated for side effects.

\* \* \* \* \*